United States Patent [19]

Green

[11] Patent Number: 5,089,009
[45] Date of Patent: Feb. 18, 1992

[54] INWARDLY BIASED SKIN FASTENER

[75] Inventor: David T. Green, Westport, Conn.

[73] Assignee: United States Surgical Corporation, Norwalk, Conn.

[21] Appl. No.: 372,025

[22] Filed: Jun. 27, 1989

[51] Int. Cl.$^5$ ................. A61B 17/00; F16B 15/00
[52] U.S. Cl. ................. 606/219; 606/220; 411/457; 411/920
[58] Field of Search ......... 128/334, 337, 335; 411/457, 920; 606/219, 220; 227/902

[56] References Cited

U.S. PATENT DOCUMENTS

| | | | |
|---|---|---|---|
| D. 286,441 | 10/1986 | Korthoff et al. | D24/27 |
| D. 286,442 | 10/1986 | Korthoff et al. | D24/27 |
| 3,209,754 | 10/1965 | Brown | 606/221 |
| 3,273,562 | 9/1966 | Brown | 606/221 |
| 3,601,302 | 8/1971 | Potekhina | 227/120 |
| 3,643,851 | 2/1972 | Green et al. | 227/19 |
| 3,757,629 | 9/1973 | Schneider | 411/920 |
| 4,217,902 | 8/1980 | March | 606/221 |
| 4,275,813 | 6/1981 | Noiles | 606/219 |
| 4,402,445 | 9/1983 | Green | 227/19 |
| 4,506,670 | 3/1985 | Crossley | 227/181 |
| 4,523,591 | 6/1985 | Kaplan et al. | 427/391 |
| 4,534,352 | 8/1985 | Korthoff | 606/220 |
| 4,583,670 | 4/1986 | Alvarado | 227/19 |
| 4,610,250 | 9/1986 | Green | 606/220 |
| 4,618,086 | 10/1986 | Li et al. | 227/19 |
| 4,635,637 | 1/1987 | Schreiber | 128/337 |
| 4,667,674 | 5/1987 | Korthoff et al. | 606/220 |
| 4,741,336 | 5/1988 | Failla et al. | 128/334 R |
| 4,841,960 | 6/1989 | Garner | 606/75 |
| 4,887,601 | 12/1989 | Richards | 606/219 |

Primary Examiner—Randall L. Green
Assistant Examiner—Gary Jackson
Attorney, Agent, or Firm—Thomas R. Bremer

[57] ABSTRACT

A surgical skin fastener with inwardly biased prongs. The fastener comprises a backspan, horizontal arms, and at least two prongs, each prong having at least one inwardly pointing barb. The prongs are resiliently biased inward for holding adjacent edges of body tissue in close contact.

17 Claims, 7 Drawing Sheets

INWARDLY BIASED SKIN FASTENER

BACKGROUND OF THE INVENTION

1. Field of the Invention

This invention relates to fasteners, and particularly to surgical fasteners used to join body tissue.

2. Description of the Prior Art

Fasteners have been used surgically to eliminate the need for suturing, which is both time consuming and inconvenient. In many applications the surgeon can use a stapler apparatus, i.e., a fastener implanting device loaded with surgical fasteners to accomplish in a few seconds what would have taken many minutes to perform by suturing. This reduces blood loss and trauma to the patient.

Surgical fasteners have been in the form of ordinary metal staples, which are bent by the delivery apparatus to hook together body tissue. Also, two-part fasteners have been used, as illustrated in U.S. Pat. No. 4,506,670 in which a barbed fastener portion is used in conjunction with a retaining piece to hold the fastener in place.

Typically, the two part fastener comprises a back span and two barbed prongs which are engaged and locked into a separate retainer piece In use, the fastener is pressed into the body tissue so that the barbs penetrate the tissue and emerge from the other side where they are then locked into the retainer piece. The retainer prevents the fastener from working loose from the tissue. The two piece fasteners usually cannot be unlocked and are not removable. For this reason, they can be made of a bioabsorbable material.

Korthoff, et al., U.S. Pat. No. 4,667,674, herein incorporated by reference, discloses a two part surgical fastener comprising a fastener member and a retainer member. The fastener member has a base, and a pair of prongs extending perpendicularly from the base. The prongs are spaced inward from the respective ends of the base in order to prevent splaying of the prongs, and to improve hemostasis.

The two piece fasteners require the staple delivery apparatus to have access to both sides of the tissue. Usually, such devices have a U-shaped member into which tissue is inserted. The stapler apparatus has a fastener holder and an anvil which are pivotally connected at one end, and mounted on the legs of the U-shaped support structure. See, for example, Green U.S. Pat. No. 4,402,445, which discloses a surgical fastener and means for applying same. In a surgical operation, the tissue to be joined is positioned between the fastener holder and the anvil, which contains the fastener retainers. The fasteners are ejected from the holder into the tissue, and the prongs are locked into the retainers.

Certain types of wounds or incisions in fascia tissue require that the two edges of the wound or incision be held together in close approximation in order to promote proper healing. The fasteners described in the above-cited patents are designed for preventing bleeding by improving hemostatis, but they are not designed for holding two edges of a wound together. Green, U.S. Pat. No. 4,610,250 discloses a two part surgical fastener in which the retainer portion has a camming surface for bending two prongs of the fastener inward. When the fastener is properly positioned across a wound the bent prongs will maintain the edges of the wound in close adjacency until the fastener is biologically absorbed. This fastener, too, requires an applying instrument to have access to both sides of the body tissue.

In some applications, however, it is not possible to have access to body tissue from two opposite directions. For example, in skin grafting applications one can only apply fasteners from a stapler positioned above the skin.

The prior art includes many examples of surgical staplers which do not enclose the body tissue between an anvil and fastener holder. For example, surgical staplers such as those described in U.S. Pat. No. 3,643,851 and U.S. Pat. No. 4,618,086 approach the skin from one direction. However, they require the use of staples which are malleable enough to be crimped by an anvil so that the prongs hook into the tissue. Typically, such staples are made of metal and are not bioabsorbable. They must be removed by another device, such as a staple extractor. Furthermore, such staples are more useful for joining tissue layers laterally, as for example in closing wounds in skin or fascia, and, although useable, they are not optimum for laminarly fastening one layer of tissue onto another as in skin grafting.

Hence there is a need for a bioabsorbable surgical fastener which is capable of being delivered into the surface of body tissue from one direction, which can join layers of tissue both laterally and laminarly as required in skin grafting applications, which provides a biasing force to hold adjacent edges of body tissue in close approximation, and which does not have to be removed from the body (a painful procedure).

SUMMARY OF THE INVENTION

Accordingly, it is one object of this invention to provide a bioabsorbable surgical fastener for joining body tissue.

It is another object of the present invention to provide a single piece fastener for joining one layer of body tissue to another layer.

It is yet a further object of the present invention to provide a surgical fastener which provides a biasing force to hold adjacent edges of body tissue in close approximation.

Still a further object of the present invention is to provide a surgical fastener in combination with an instrument for applying same.

These and other objects and advantages are achieved herein by providing a surgical fastener for joining body tissue, said surgical fastener comprising:

a) a backspan comprising a bridge member; and b) at least two prongs depending from the backspan, said prongs being in oblique orientation to each other in which the distal ends of said prongs are inclined towards each other, said prongs being movable in response to pressure to a substantially parallel orientation to each other, and being resiliently returnable to said oblique orientation when said pressure is removed.

The surgical fastener of the present invention is optimally constructed of a bioabsorbable resinous material. A preferred resinous material, which is absorbable in the body, is disclosed in Kaplan et al., U.S. Pat. No. 4,523,591, hereby incorporated by reference.

Further features of the invention, its nature and various advantages will be more apparent from the accompanying drawings and the following detailed description of the invention.

BRIEF DESCRIPTION OF THE DRAWINGS

FIG. 2b illustrates a top view of the alternative embodiment;

FIG. 2c illustrates a bottom view of the alternative embodiment;

DETAILED DESCRIPTION OF THE INVENTION

Figure 1A:
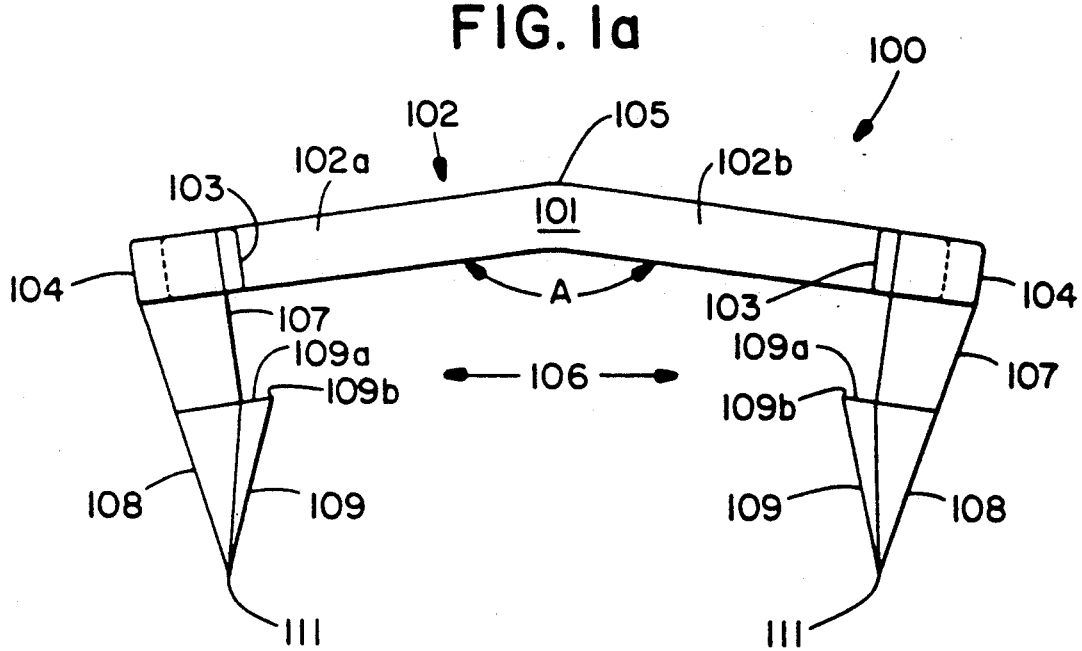
FIG. 1a illustrates a front view of the inwardly biased skin fastener.
Figure 1B:
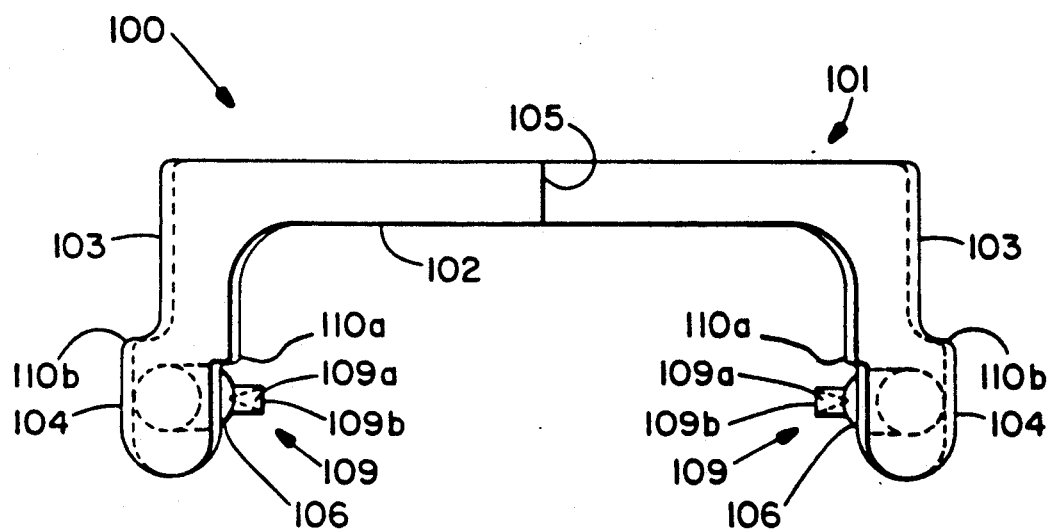
FIG. 1b illustrates a top view of the inwardly biased skin fastener.
Figure 1C:
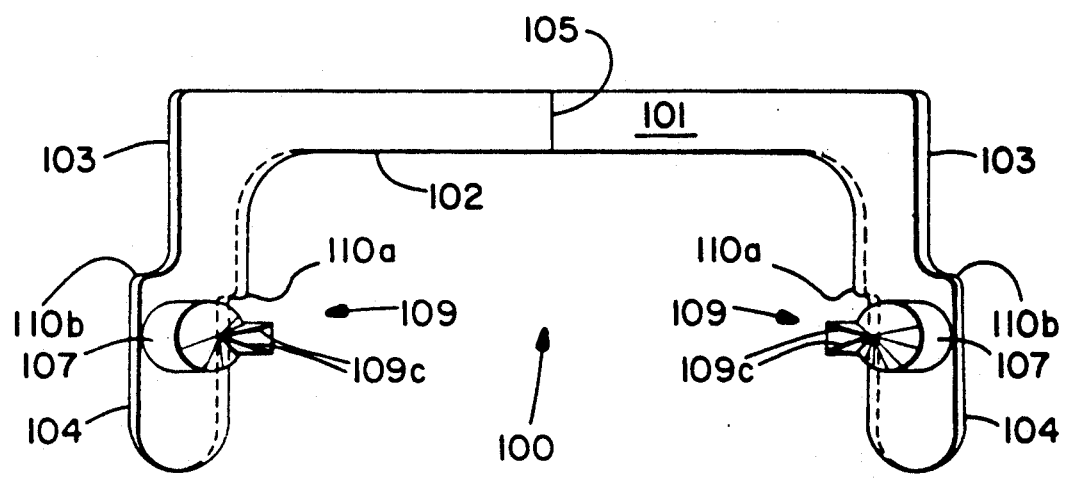
FIG. 1c illustrates a bottom view of the inwardly biased skin fastener.
Figure 1D:
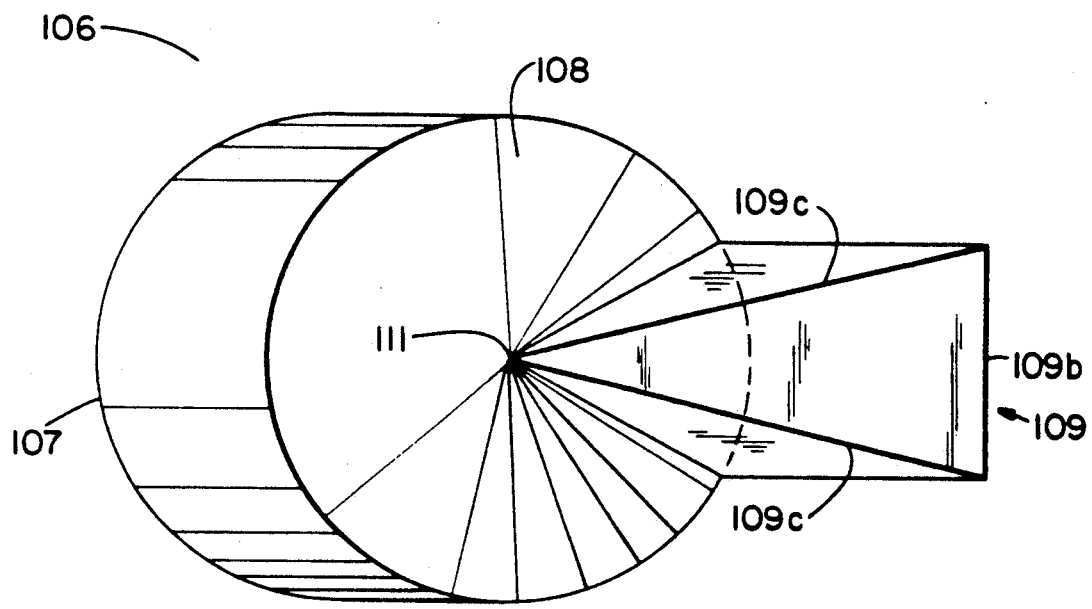
FIG. 1d illustrates a detailed bottom view of the prong and barb.

The skin fastener disclosed herein can be used in conjunction with a surgical fastener applying instrument capable of propelling or implanting the skin fastener into the body tissue to be fastened. Generally such instruments will have a chamber for holding one or more fasteners, a means for storing and releasing power such as a spring or compressed gas, and a trigger means.

FIGS. 1a, 1b, 1c and 1d illustrate one embodiment of the present invention. Fastener 100 comprises a backspan 101 and barbed prongs 106. Backspan 101 comprises a bridge portion 102, and preferably at least two arm members 103 extending substantially parallel to each other and transversely in a horizontal direction from bridge 102, each arm extending from the same side of the bridge portion. The arms 103 each comprise an end portion 104 which are in the same plane as the arms, but the end portions 104 are offset in a direction away from each other so that the distance between the end portions 104 is slightly greater than the distance between the arms 103. The arms 103 are the same width as the end portion 104. Thus, offsetting the end portions produces an inner ridge 110a and an outer ridge 110b. Arms 103 are optional preferred features which provide an offset to facilitate ejection of the fastener from a fastener applying instrument. Armless fasteners are discussed below.

As explained above, in operations such as skin grafting wherein layers of tissue are fastened edge to edge or in closing wounds and incisions, it is desirable to have a lateral force to keep the edges of tissue in close contact. This is accomplished in the present invention by providing a fastener with inwardly biased prongs. In the present embodiment such biasing is accomplished by the bend or flexure 105 midway in the bridge portion 102 of the backspan 101. Bend 105 defines two symmetrical anticlinal wing portions 102a and 102b. As can be seen in FIG. 1a, the bridge 102 is bent at an angle A less than 180°, i.e., the wing portions 102a, 102b each decline between 5° to 25° and optimally 8°22′ from the horizontal. Prongs 106 depend from end portions 104 at right angles to the end portions 104 and arms 103. But since the bridge 102 is slightly bent at flexure 105 the prongs 106 are not parallel to each other. Rather, the prongs are biased inward such that the distal ends of the prongs are closer to each other than the proximal end. As will be explained more fully below, the fastener functions like a spring clamp to hold the edges of the tissue together.

Each prong 106 comprises a shaft 107, and tip 108 which optimally tapers into a sharp point 111. Shaft 107 is slightly tapered from an oval cross section near the backspan 101, to a circular cross section at the tip 108.

Each prong 106 has at least one substantially triangular shaped barb 109 which is flat on both sides to minimize body tissue resistance. Each barb 109 is mounted on the interior side of the prong 106 such that they face each other. The blade-like barbs 109 of the present fastener 100 not only puncture body tissue, but also slice through the tissue, thereby easing the entry of the fastener. The barbs 109 are in coplanar alignment with respect to each other. Barbs 109 each have a flat back surface 109a and vertex 109b to provide resistance to backward movement of the fastener 100. Once implanted, fastener 100 cannot be easily removed. Barbs 109 also have cutting edges 109c to facilitate implantation by slicing through body tissue.

Figure 2A:
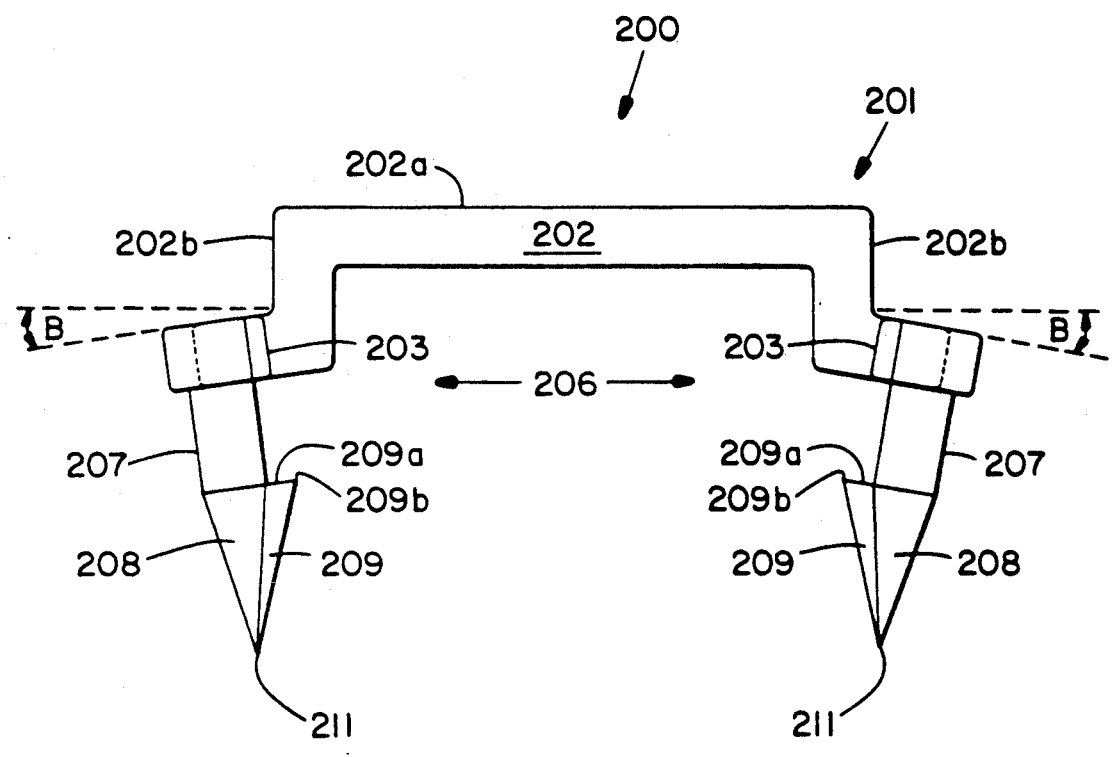
FIG. 2a illustrates a front view of an alternative embodiment of the present invention.

Referring now to FIGS. 2a, 2b and 2c which show respectively the front side view, top and bottom views of an alternative embodiment 200 of the present invention, backspan 201 differs from the previously described embodiment in that backspan 201 has a U-shaped bridge 202 with a top beam 202a, and downwardly extending sidewalls 202b. Top beam 202a does not have a biasing bend or flexure similar to flexure 105 in bridge 102. Instead, the top beam 202a is straight. Arms 203 of backspan 201 are tilted from horizontal, however, at an angle B which is optimally 5° to 25° such that the prongs 206 are biased inward. The side walls 202b allow an expansion space under the top beam 202a in order to allow for swelling of the body tissue.

As in the previously described embodiment, arms 203 have end portions 204 which are offset a small distance outwardly, and away from each other, thereby creating inner ridges 210a and outer ridges 210b. Also, arms 203 are preferable, but optional, features of the fastener 200.

Prongs 206 depend from end portions 204 at substantially right angles to the end portions 204. Each prong 206 comprises a shaft 207 and tip 208 which optimally tapers to a sharp point 211. Furthermore, as in the previously described embodiment, each prong 206 has at least one substantially triangularly shaped barb 209 which is flat on both sides. Each barb 209 is mounted on the interior side of the prong 206. The blade like barbs 209 not only puncture body tissue, but also slice through the tissue, thereby facilitating the entry of the fastener. The barbs 209 are in coplanar alignment with respect to each other.

Barbs 209 each have a flat back surface 209a and vertex 209b to provide resistance to the backward movement of the fastener 200. Once implanted, fastener 200 cannot be easily removed. Barbs 209 also have cutting edges 209c to facilitate implantation of the fastener 200 by slicing through body tissue.

Because the fasteners disclosed herein are not adapted to be removable they are preferably made of bioabsorbable material such as copolymers of lactide and glycolide, or other bioabsorbable polymer materials. A preferred bioabsorbable resinous material for constructing fasteners 100 and 200 is disclosed in Kaplan et al. U.S. Pat. No. 4,523,591, herein incorporated by reference. Fasteners of the present invention may be formed as integral, single piece constructions by injection molding. The material of construction for fasteners 100 and 200 must have a degree of resiliency or springiness sufficient to allow bending or flexing of the fasteners 100 or 200 from the initial angled position to a straight position when they are implanted. When being driven by a fastener implanting instrument the backspan 101 or 201 will straighten such that the prongs 106 or 206 will enter the body tissue perpendicularly. When the driving force is removed the resiliency of the construction material will urge the fastener back into the initially bent position thereby biasing the prongs 106 or 206 inwardly. When implanted across a wound or an incision the fasteners will exert a lateral inward force to clamp the two edges of the tissue together.

Figure 3:
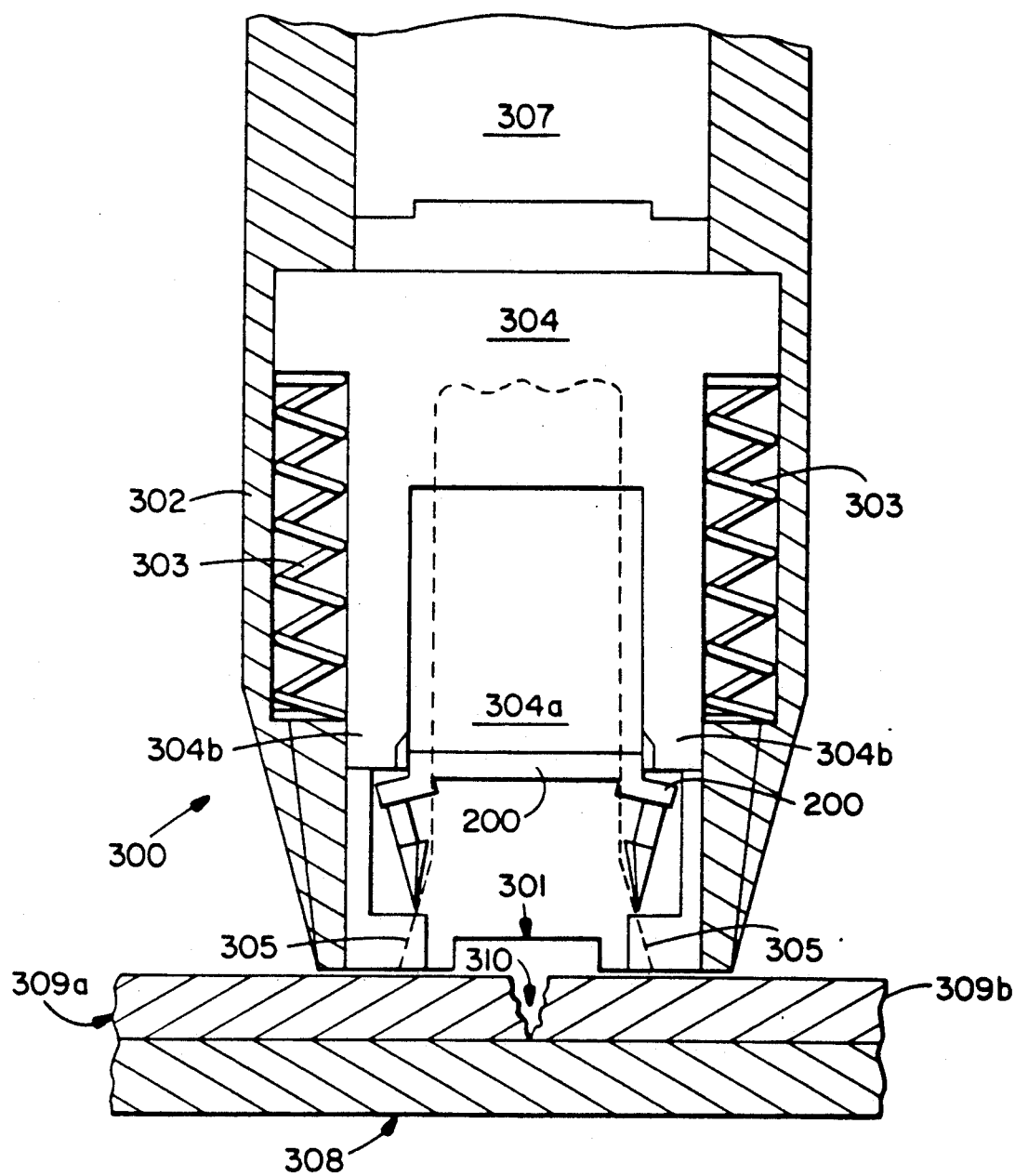
FIG. 3 illustrates a diagrammatic view of a skin fastener of the present invention in conjunction with the firing chamber of a fastener implanting instrument.
Figure 3:
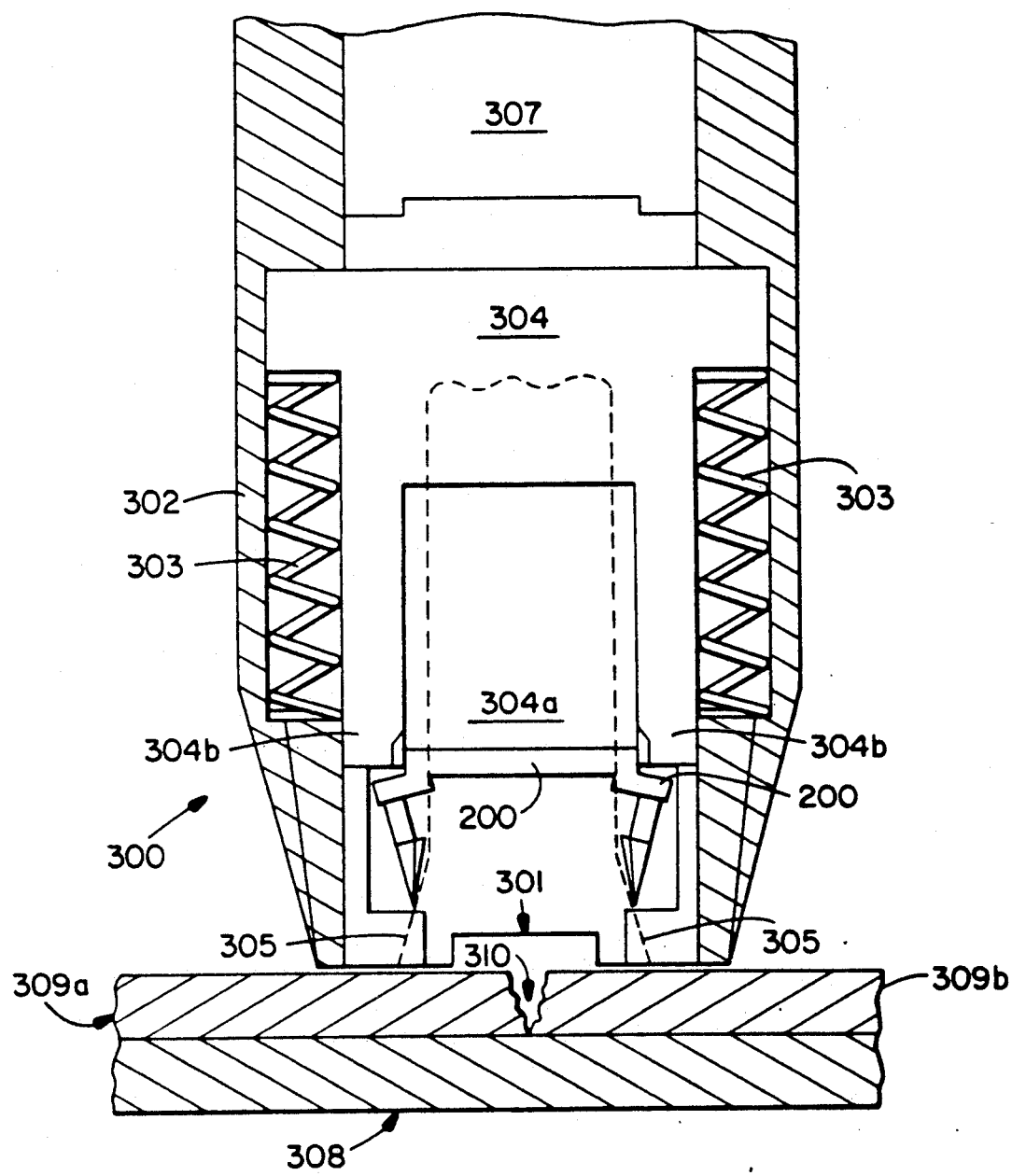

FIG. 3 illustrates a fastener 200 in combination with a pusher mechanism of a fastener applying instrument 300. The instrument walls 302 enclose a pusher plate 304 having a backspan pusher member 304a and a pair of arm pusher members 304b. Pusher plate 304 is adapted to contact the top surface of the backspan and arms as the fastener 200 is being implanted. Driver 307 is adapted to drive the pusher plate 304. Resilient springs 303 return the pusher plate 304 to the initial pre-firing position after the fastener 200 has been ejected Camming surfaces 305 contact the barbs and bias the prongs into a substantially parallel orientation with respect to each other and a substantially perpendicular orientation with respect to the body tissue 308. The offset provided by the arms 103, and 203 permit the prongs to be cammed into a vertical position and parallel orientation without interfering with the downward movement of the fastener. Exit opening 301 allows egress of the fastener 200. Fastener 200 (or alternatively fastener 100) can be used to fasten body tissue laterally as, for example, in closing wound 310 between tissue layers 309a and 309b, and it can also be used to fasten body tissue laminarly, as for example in grafting body tissue layers 309a and 309b onto body tissue layer 308.

The prongs of the above described fasteners, are oriented obliquely to each other such that the distal ends of the prongs are inclined towards each other. The oblique orientation of the prongs can be provided by flexure 105 or by a tilt in the arm members 203, as mentioned above. The fastener has sufficient flexibility to enable the prongs to move to a substantially parallel orientation to each other when pressure is applied, for example by camming surface 305. Straightening the prongs to a parallel orientation permits the fastener to enter the body tissue more easily. When the fastener has been implanted and is no longer contacted by the camming surface, the resiliency of the fastener urges the prongs back into their initial oblique orientation, thereby acting as a spring clamp to close up wounds in tissue and hold the edges of torn body tissue in close adjacency for quicker and easier healing. Barbs are located on the inside surface of the prongs to grip the body tissue more securely.

Figure 4:
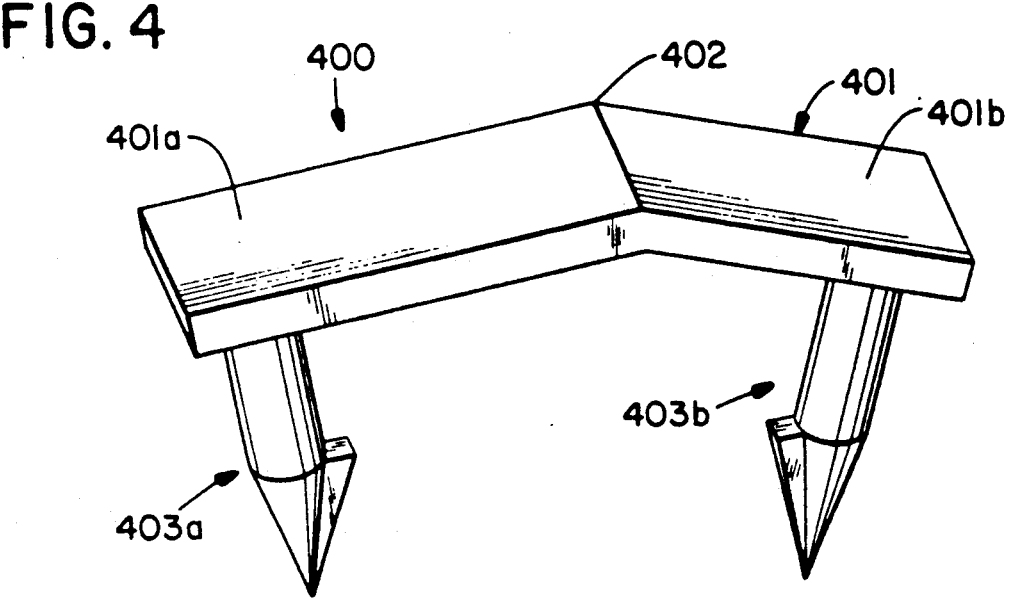
FIGS. 4 and 5 illustrate perspective views of alternative embodiments of the inwardly biased skin fastener which do not possess arm members.
Figure 5:
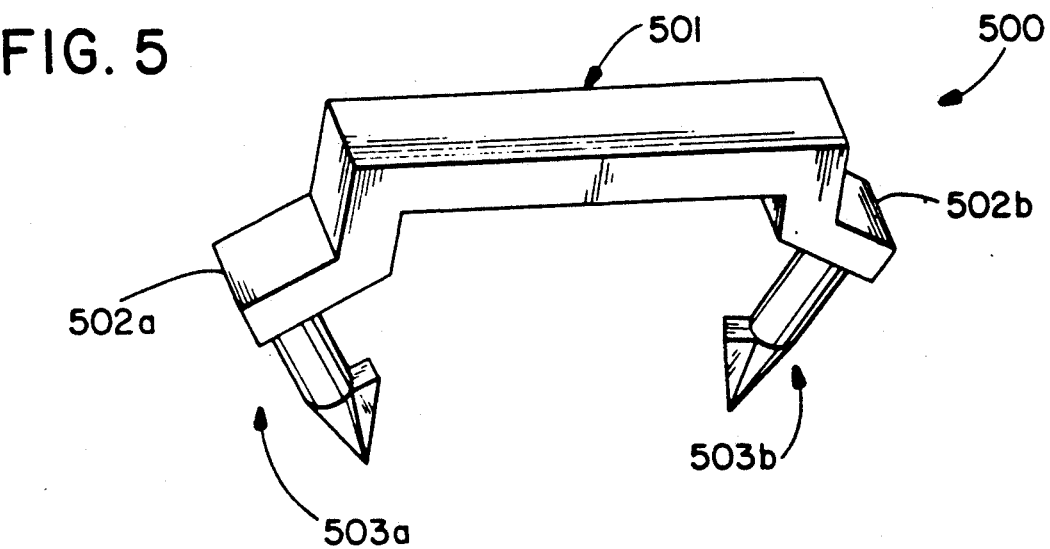

As can be seen in FIGS. 4 and 5 the inwardly biased skin fastener can be constructed without arms 103 or 203, although the arms are preferable because they provide an offset to facilitate camming the prongs to a vertical position in the fastener applying instrument. Armless fastener 400 defines a single vertical plane, and is an armless alternative embodiment to fastener 100. Backspan 401 is divided into anticlinal portions 401a and 401b, by a central bend 402. Prongs 403a and 403b depend perpendicularly from their respective portions of the backspan, and their distal ends are biased towards each other by means of the bend 402 in the backspan. Armless fastener 500 also defines a single plane, but it has a U-shaped backspan 501, inclined end portions 502a and 502b, and prongs 503a and 503b, which are inclined so that their respective distal ends are biased towards each other.

The surgical fasteners of the present invention can be made of any size suitable to the purpose of fastening body tissue. Generally, the backspan may be about 7 to 10 mm in length, for example, and the prongs may be about 3 to 5 mm long. The arms may be about 2 to 4 mm from the backspan to the prong. Other dimensions may be used in accordance with the different types of applications intended.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical fastener for joining body tissue, said surgical fastener comprising:
   a) a backspan comprising a bridge member, said backspan additionally having at least two arms extending substantially horizontally from said backspan in substantially parallel orientation to each other; and
   b) at least two prongs depending from the backspan, said prongs being in oblique orientation to each other in which the distal ends of said prongs are inclined towards each other, said prongs being movable in response to pressure to a substantially parallel orientation to each other, and being resiliently returnable to said oblique orientation when said pressure is removed.

2. The surgical fastener of claim 1 wherein the bridge member is an inverted U-shaped structure, and said arms are inclined with respect to said backspan.

3. The surgical fastener of claim 1 wherein said arms are inclined from about 5° to about 25° from the horizontal.

4. In combination with a surgical apparatus for implanting a surgical fastener into body tissue, said surgical apparatus comprising a chamber for holding at least one surgical fastener, means for storing and releasing power, and trigger means, a surgical fastener comprising:
   a) a backspan comprising a bridge member and at least two arms extending substantially horizontally from said backspan in substantially parallel orientation to each other; and
   b) at last two prongs depending from said backspan, said prongs being in oblique orientation to each other in which the distal ends of said prongs are inclined towards each other, said prongs being movable in response to pressure to a substantially parallel orientation to each other, and being resiliently returnable to said oblique orientation when said pressure is removed.

5. The combination of claim 4 wherein the surgical fastener is constructed from bioabsorbable material.

6. The combination of claim 5 wherein the bioabsorbable material is a copolymer of glycolide and lactide.

7. The combination of claim 4 additionally comprising at least one substantially triangular shaped barb on each prong, said prongs being located on the interior side of their respective prongs.

8. The combination of claim 7 wherein said barbs are substantially flat, and in coplanar alignment with respect to each other.

9. The combination of claim 4 wherein the bridge member is an inverted U-shaped structure, and said arms members are inclined with respect to said backspan.

10. The combination of claim 9 wherein said arms are inclined from about 5° to about 25° from the horizontal.

11. The combination of claim 4 wherein the bridge member comprises a central bend defining two anticlinal portions.

12. The combination of claim 11 wherein the anticlinal portions define an angle of less than 180°.

13. The combination of claim 4 wherein the surgical fastener is constructed from a resilient material.

14. The combination of claim 4 wherein the surgical fastener is integrally constructed from a polymeric material.

15. The combination of claim 4 wherein the surgical apparatus further comprises camming means for moving the prongs of said surgical fastener from the oblique orientation to the parallel orientation.

16. The combination of claim 15 wherein said camming means comprises at least one camming surface.

17. A method of joining body tissue comprising:
 a) providing a surgical fastener having
   (i) a backspan comprising a bridge member; and
   (ii) at least two prongs depending from said backspan, said prongs being in oblique orientation to each other with the distal ends of said prongs inclined towards each other, said prongs being movable in response to pressure to a substantially parallel orientation to each other for insertion into body tissue, and being resiliently returnable to said oblique orientation when said pressure is removed;
 b) applying pressure to move said prongs into substantially parallel orientation;
 c) inserting said prongs into body tissue; and
 d) releasing said pressure so that said prongs are resiliently biased toward said oblique orientation to hold the body tissue together.

* * * * *